United States Patent [19]
Axe et al.

[11] Patent Number: 5,203,343
[45] Date of Patent: Apr. 20, 1993

[54] METHOD AND APPARATUS FOR CONTROLLING SLEEP DISORDER BREATHING

[75] Inventors: John R. Axe; Khosrow Behbehani, both of Arlington; John R. Burk, Aledo; Edgar A. Lucas, Fort Worth; Fu-Chung Yen, Arlington, all of Tex.

[73] Assignee: Board of Regents, The University of Texas System, Austin, Tex.

[21] Appl. No.: 715,374

[22] Filed: Jun. 14, 1991

[51] Int. Cl.$^5$ .............................................. A61B 5/08
[52] U.S. Cl. .................................. 128/725; 128/848; 128/716
[58] Field of Search ............... 128/721, 716, 724, 725, 128/848

[56] References Cited

U.S. PATENT DOCUMENTS

| | | | |
|---|---|---|---|
| Re. 33,442 | 11/1990 | George | 128/860 |
| 3,882,847 | 5/1975 | Jacobs . | |
| 4,365,636 | 12/1982 | Barker | 128/716 |
| 4,414,982 | 11/1983 | Durkan | 128/716 |
| 4,449,526 | 5/1984 | Elam | 128/206.21 |
| 4,484,578 | 11/1984 | Durkan | 128/204.24 |
| 4,506,666 | 3/1985 | Durkan | 128/204.23 |
| 4,537,190 | 8/1985 | Caillot et al. | 128/204.22 |
| 4,570,631 | 2/1986 | Durkan | 128/204.23 |
| 4,630,614 | 12/1986 | Atlas | 128/721 |
| 4,655,213 | 4/1987 | Rapoport | 128/205.25 |
| 4,686,975 | 8/1987 | Naimon et al. | 128/204.23 |
| 4,773,411 | 9/1988 | Downs | 128/204.18 |
| 4,782,832 | 11/1988 | Trimble et al. . | |
| 4,823,788 | 4/1989 | Smith et al. | 128/205.24 |
| 4,830,008 | 5/1989 | Meer | 128/421 |
| 4,870,963 | 10/1989 | Carter | 128/205.24 |
| 4,878,502 | 11/1989 | Dietz | 128/725 |
| 4,883,050 | 11/1989 | Urman et al. | 128/202.27 |
| 4,919,128 | 4/1990 | Kopala | 128/207.18 |
| 4,944,310 | 7/1990 | Sullivan | 128/848 |
| 4,971,051 | 11/1990 | Toffolon | 128/206.26 |
| 5,002,050 | 3/1991 | McGinnis | 128/204.18 |
| 5,007,420 | 4/1991 | Bird | 128/200.14 |
| 5,009,635 | 4/1991 | Scarberry | 604/27 |
| 5,038,771 | 8/1991 | Dietz | 128/204.21 |
| 5,038,773 | 8/1991 | Norllen et al. | 128/205.23 |
| 5,065,756 | 11/1991 | Rapoport | 128/204.18 |
| 5,074,297 | 12/1991 | Venegas | 128/204.18 |
| 5,095,900 | 3/1992 | Fertig et al. | 128/207.14 |
| 5,103,814 | 4/1992 | Maher | 128/204.18 |

FOREIGN PATENT DOCUMENTS 8810108 12/1988 World Int. Prop. O. .......... 128/725

OTHER PUBLICATIONS

*Effect of positive nasal pressure on upper airway pressure flow relationships*, Schwartz et al., Johns Hopkins School of Medicine, ©1989 American Physiology Society.

"Positive nasal airway pressure eliminates snoring as well as obstructive sleep apnea", Richard B. Berry and A. Jay Block, Chest, 85, 11 Jan. 1984.

(List continued on next page.)

*Primary Examiner*—Lee S. Cohen
*Assistant Examiner*—Robert L. Nasser, Jr.
*Attorney, Agent, or Firm*—James E. Bradley

[57] ABSTRACT

A method and device for controlling sleep disorder breathing utilizes variable pressure. The compressor supplies air at a relatively low pressure to the user's air passages while the user is asleep. A pressure transducer will monitor the pressure and convert the pressure into an electrical signal. The electrical signal is filtered and processed to compare it to the characteristics of waveforms that exists during snoring. If the envelope of the waveform exceeds an average threshold value in duration and in area, then the microprocessor will consider the envelope possibly associated with a snore. If a selected number of envelopes of this nature occur within a selected time period, then the microprocessor considers snoring to exist and increases the pressure of the compressor. If snoring is not detected within a certain time period, then the microprocessor lowers the level gradually.

7 Claims, 1 Drawing Sheet

OTHER PUBLICATIONS

*Snoring: Clinical implication and treatment,* Rice, Dale H. and Michael Pesky, Otolaryngology-Head and Neck Surgery, 95:28, 1986.

J. E. Remmers et al., "Pathogenesis of upper airway occlusion during sleep," Dept. of Medicine, Physiology, and Anatomy, Univ. of Texas Medical Branch, 1978.

Technical Note, MESAM, A heart rate and snoring recorder for detection of obstructive sleep apnea, Sleep, vol. 13, No. 2, 1990.

"Snoring and its Treatment", *British Medical Journal,* London-Saturday Aug. 11, 1984, vol. 289, No. 6441, 335–336.

K. Behbehani, T. Kang, A Microprocessor-Based Sleep Apnea Ventilator (2 pp.).

METHOD AND APPARATUS FOR CONTROLLING SLEEP DISORDER BREATHING

BACKGROUND OF THE INVENTION

1. Field of the invention

This invention relates in general to a method and apparatus for controlling sleep disorder breathing, particularly one utilizing positive air pressure supplied to a person's air passages.

2. Description of the Prior Art

The majority of patients diagnosed at sleep disorders centers in the United States suffer from excessive daytime sleepiness. The leading cause of this symptom is sleep apnea.

Sleep apnea is a potentially lethal condition characterized by multiple obstructive or mixed apneas during sleep. Symptoms are repetitive episodes of inordinately loud snoring and excessive daytime sleepiness. The characteristic snoring pattern noted with this syndrome is one in which inspiratory snores gradually increase when obstruction of the upper airway develops. A loud, choking inspiratory gasp then occurs as the patient's respiratory efforts succeed in overcoming the occlusion. The aroused patient is usually aware of neither the breathing difficulty nor of the numerous accompanying body movements that at times violently disturb his sleep. A diagnostic study is necessary for an adequate description of the patient's sleep breathing pattern.

Apneic episodes during sleep are defined as cessations of air flow at nose and mouth lasting 10 seconds or longer and can be readily documented by polysomnographic recordings. Variations in night-to-night frequency of apneic pauses exist in many patients, with increased frequency appearing to follow upper respiratory infections or use of sedating drugs or alcohol.

Treatments available for sleep apnea vary from weight loss to surgical intervention to prosthetic devices. Although weight loss is the most desirable approach, few patients are able to comply with their diets and very few can afford to continue the exposure to the symptoms of sleep apnea for six months to a year while losing sufficient weight to reduce or cure the disease. Surgical approaches are only effective in about 50% of the cases, are invasive, expensive and may produce undesirable side effects.

The most successful prosthetic device has been the nasal continuous positive airway ventilator ("CPAP"). It was initiated by a group in Australia who adapted a vacuum sweeper motor to a hose and attached it to the patient's face via a nasal mask. The advantages of the nasal CPAP system are that it produces immediate relief, is non-invasive and can be used while achieving weight loss and thus eliminating the need for surgery. The primary problem with nasal CPAP has been compliance. While nearly all of patients are fitted with nasal CPAP as an initial treatment modality, many cease using the system after about six months.

Investigation of the causes for poor compliance among patients has identified three primary factors. The first factor is the lack of perfect fit and discomfort of wearing the nasal mask. The positive pressure of the ventilator flow is often mentioned as the second factor. Some patients experience an uncomfortable and annoying sensation of forced air stream in their nose and mouth. Third, dry mouth and throat are often cited as the source of dissatisfaction with the sleep apnea ventilators.

Hypopnea is a milder form of apnea, usually referring to episodes of partial obstruction of the upper airway passages. Excessive snoring, without hypopnea or apnea occurrences, can also be a serious problem. Apnea, hypopnea, and snoring will be referred to herein as sleep disorder breathing.

SUMMARY OF THE INVENTION

The method and apparatus of this invention involves utilizing forced air pressure through a tube to the person's airway passages. Initially, the air is supplied at a relatively low pressure. A pressure transducer monitors the air pressure to detect the onset of sleep disorder breathing, particularly snoring. If a detection occurs, a microprocessor will increase the air pressure for a selected time. Then, if no other snoring is detected, the microprocessor will gradually reduce the air pressure back to the initial level. If additional snoring is detected, the air pressure will be increased at stages until the snoring ceases to exist.

In the preferred embodiment, the onset of sleep disorder breathing is detected by monitoring pressure waveforms which occur as a result of a person's breathing. Apnea and hypopnea are normally preceded by snoring. The snoring creates an identifiable waveform. The microprocessor will compare the waveforms resulting from the person's breathing to characteristics of a snoring waveform. If the comparison indicates that snoring exists, then the air pressure will be increased to avoid the onset of sleep disorder breathing.

A filter will pass only those waveforms which have frequencies associated with snoring. This signal is rectified and passed through a peak detector to determine an envelope associated with the waveform. An analog to digital converter digitizes the waveform.

The microprocessor compares the energy level or area of the envelope to the average for that person. This is handled by summing the amplitudes of the samples within the envelope and comparing this number to an average of the middle eight of the past ten values. The microprocessor will also compare the duration of the present envelope to an average of the middle eight of the past ten values. If the present area and duration are greater than a selected fraction of the past averages, then the microprocessor will count the waveform as a snore that might be associated with sleep disorder breathing.

If a selected number of the snore waveforms are counted within a selected time period, then the microprocessor increases the positive air pressure to a first level. If snoring continues, the microprocessor will increase the air pressure to higher levels. At a maximum level, an alarm can be actuated. If after a certain time period, no additional snoring is detected, the microprocessor will reduce the air pressure incrementally in a controlled sequence.

DETAILED DESCRIPTION OF THE INVENTION

Figure 1:
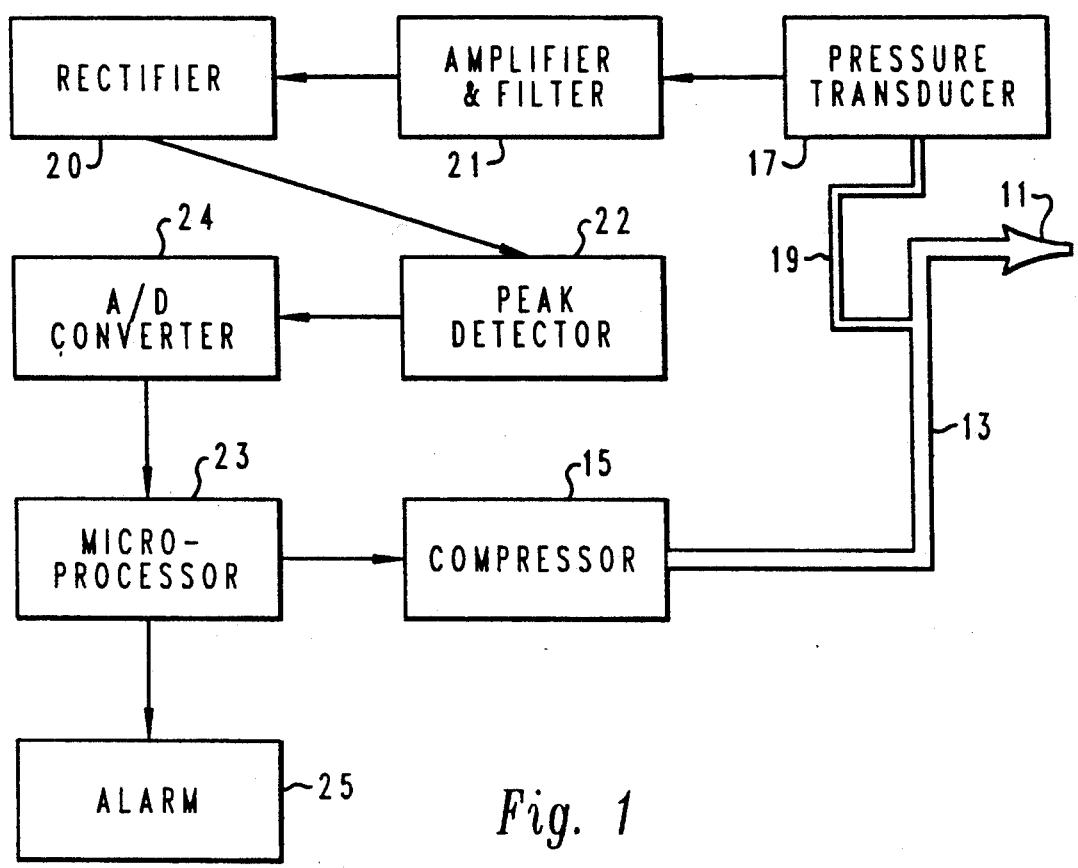
FIG. 1 is a block diagram illustrating the method and apparatus of this invention.

Referring to FIG. 1, the apparatus will include a nostril adapter 11. Nostril adapter 11 is a commercially available product that has two nozzles, each of which fits within a nostril (not shown) of a user. Adapter 11 connects to a flexible tube 13 that leads to a low pressure compressor 15. Adapter 11 and tube 13 make up an interface for supplying air pressure to the user. Compressor 15 draws in ambient air and will compress it to a variable pressure which can be selected. Increasing the pressure will increase the flow rate of the air through the tube 13.

A conventional pressure transducer 17 is connected by a pneumatic tube 19 to the tube 13 for sensing pressure in the tube 13. Pressure transducer 17 will monitor the dynamic pressure that exists in the interface comprising the tube 13 and adapter 11. This pressure is substantially the same as in the upper airway passages of the user. The pressure within the tube 13 will depend not only on the compressor 15, but also on the user's breathing. The pressure transducer 17 will monitor all of the waveforms and convert these pressure changes into analog electrical signals.

Figure 2:
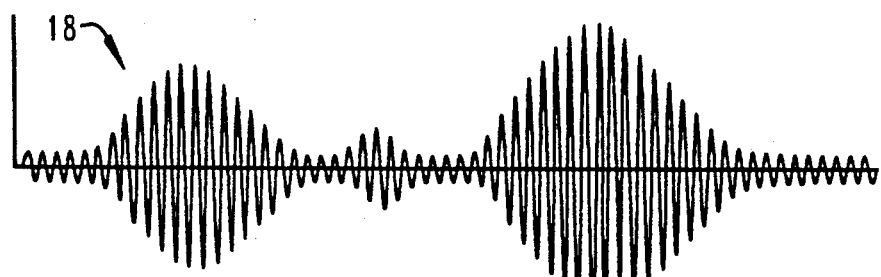
FIG. 2 is an illustration of a typical analog signal of a pressure waveform associated with snoring after filtering out frequencies of no interest with the apparatus of FIG. 1.

The signals from the pressure transducer 17 pass to an electronic amplifier and filter 21 of conventional design. After amplification, filter 21 will block frequencies received from the pressure transducer 17 that are not associated with snoring waveforms. Laboratory tests have determined that the waveforms associated with snoring will have frequencies within the range of about 20 HZ to 120 HZ. These signals are passed and the rest blocked. FIG. 2 illustrates a typical analog electrical signal 18 after passing through filter 21 that would indicate snoring. The frequencies within the waveforms of signal 18 are within 20 to 12.0 HZ.

The filtered signals 18 are rectified by a conventional rectifier 20 and passed to a conventional peak detector 22. Peak detector 22 will detect the contours of the waveforms of the signal 18. The result is digitized by a conventional analog to digital converter 24.

Figure 3:
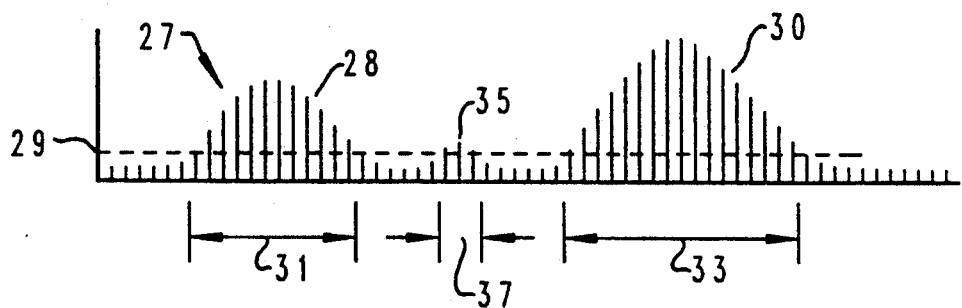
FIG. 3 is a graph illustrating pressure waveform of FIG. 2, after it has been rectified, past through a peak detector and digitized by the apparatus illustrated in FIG. 1.

FIG. 3 illustrates the results, with waveform 27 being processed from the analog waveform 18 of FIG. 2. There are two large envelopes 28 and 30 and a smaller envelope 35. The vertical lines within the envelopes 28, 30 and 35 represent samples taken of the amplitudes at constant time intervals. Preferably, there are 100 samples taken per second, with each sample having an amplitude that is proportional to a particular point on the envelopes 28, 30 and 35.

A noise threshold 29 will be selected to eliminate signals having amplitudes below a selected level. The numerals 31, 33 and 37 represent the durations in real time of the envelopes 28, 30 and 35. The durations 31, 33, 37 begin and end at the points where the envelopes 28, 30 and 35 intersect the noise threshold line 29. Laboratory tests have determined that a typical waveform associated with a snore lasts about 0.4 seconds.

The microprocessor 23 computes running averages of durations of past waveforms detected beginning with the particular session with that user. Preferably, the microprocessor 23 will maintain values of the past ten durations, average the middle eight values, and multiply the average by a fraction to determine a threshold average, which is preferably 60 percent of the computed average. If the present duration exceeds the threshold average, it will be noted. If not, the microprocessor 23 will consider the present envelope to be other than associated with snoring.

For example, the duration 31 likely might exceed 60 percent of the average. If duration 31 has a value within the middle eight of the last ten, a new average will be computed to compare with duration 37. Duration 37 will likely not meet the threshold test, therefore envelope 35 will not be counted as a snoring waveform. Even if duration 37 does not fall within a middle eight values of the last ten durations, it will be considered when computing new threshold averages for subsequent envelopes.

Also, the energy level will be computed for each envelope 28, 30, 35. The energy level is the area of each envelope 28, 30, 35. The area is the summation of the amplitudes of the vertical sample lines within the durations 31, 33, 37. Similarly, the microprocessor 23 computes an area average based on the middle eight values of the last ten areas. The average threshold area is preferably 60 percent of this average. The present area is compared to the average threshold area. If the present envelope has an area that exceeds the average threshold area, and if the present envelope has a duration that exceeds the average threshold duration, the microprocessor 23 will enter a count. The present area will be considered when updating the average threshold area for subsequent envelopes, even if the present area did not exceed the average threshold.

The threshold area and the threshold durations are reduced by 20 percent if no snoring waveforms are detected within a one minute period. The 20 percent reduction in threshold area and duration occurs each one minute period that is free of snoring waveforms until a selected minimum for each is reached.

The envelopes 28 and 30 will likely result in a count for each. The small envelope 35 located between the two envelopes 28, 30 will likely not be counted. The microprocessor 23 will continue to make counts when the areas and durations exceed the threshold values, with the threshold values continuously being updated.

If the counts of envelopes that meet the threshold values reach a selected number within a certain time period, then the microprocessor 23 will recognize this as sleep disorder breathing snoring. In the preferred embodiment, there must be a snoring waveform that is counted within 30 seconds from the termination of the last snoring waveform counted. Three of these counts must occur before the microprocessor 23 recognizes this as sleep disorder breathing snoring. For example, if envelopes 28 and 30 met the threshold area and duration values, but envelope 35 did not, then envelope 30 would need to commence within 30 seconds of the termination of envelope 28. Also, another envelope that met the threshold values would have to occur within 30 seconds of the termination of the envelope 30. The termination and commencement points are the points where the envelopes pass the noise threshold line 29.

Initially, the compressor 15 will be operating at a minimum pressure, for example 5 cm of water. If sleep disorder breathing snoring is detected, as described above, the microprocessor 23 will increase the pressure of compressor 15 by an increment. For example, initially the increase might be 2 cm of water. If after the initial increase of pressure, sleep disorder breathing snoring is still detected by three snoring envelope counts within 30 second time periods of each other, the microprocessor 23 will again increase the pressure by another 2 cm of water. This incremental increase can go on until a maximum pressure level has been reached. Preferably the maximum level is about 15 cm of water. If the maximum level does not stop the snoring being detected, then an alarm 25 will be signaled to sound an alarm.

If during a 20 minute interval, no more sleep disorder breathing snoring is detected by microprocessor 23, the microprocessor 23 will direct the compressor 15 to decrease in a controlled manner. The compressor 15 will decrease in one embodiment about one cm of water pressure during every 20 minute interval in which no sleep disorder breathing snoring is detected.

In operation, a user's breathing will create a generally sinusoidal curve within interface 1 which includes adapter 11 and tube 13 that represents the intake and expelling of air. Tests have determined that the pressure waveform will be modulated if a person begins to snore. Snoring creates a wave pattern that has an identifiable frequency. Snoring thus creates a waveform that can be distinguished from other fluctuations in the pressure which might be due to coughing, body movement and the like. Laboratory tests have also determined that a positive flow of air into the user's airway passages will in many cases cause the snoring to cease and also will avoid the occurrence of sleep disorder breathing such as apnea and hypopnea.

Compressor 15 will supply air pressure to the user through tube 13 at a selected minimum level. Pressure transducer 17 will monitor the air pressure. Filter 21 will amplify and pass only waveforms 18 having frequencies of interest, as illustrated in FIG. 2. The signals are conditioned by the rectifier 20, peak detector 22 and A/D converter 24 to the form shown in FIG. 3. The durations 31, 33 and 37 of envelopes 28, 30 and 35 will be compared to a running average threshold value. The areas or energy levels of the envelopes 28, 30 and 35 will be computed and compared to a running average threshold value.

If the present values of the durations 31, 33, 37 and areas exceed the minimum threshold averages, then the envelopes 28, 30 and 35 will be counted as waveforms associated with sleep disorder breathing. If a selected number of the waveforms associated with snoring are counted within a certain time period of each other, then the microprocessor will cause the compressor 15 to increase its pressure for a certain time period.

If after a selected time, no further sleep disorder breathing snoring is detected, the microprocessor 23 will cause compressor 15 to decrease its pressure. If sleep disorder breathing snoring continues, the microprocessor 23 will cause the compressor 15 to further increase its pressure up to a maximum level.

The invention has significant advantages. The low air pressure utilized while sleep disorder breathing is not occurring is much more comfortable to the user than the higher pressures required continuously during the prior art systems. If the system fails to stop the snoring, thereby indicating sleep disorder breathing, an alarm can be sounded to wake other people or the person to avoid a potentially dangerous situation. The system automatically adapts to the level of air flow required by the user during the night.

While the invention has been shown in only one of its forms, it should be apparent to those skilled in the art that it is not so limited but is susceptible to various changes without departing from the scope of the invention. For example, humidity and temperature control devices may be incorporated to further the comfort to the user.

We claim:

1. A method for controlling sleep disorder breathing of a person, comprising:
   connecting an interface from a source of air pressure to the person's nostril passages;
   supplying air pressure from the source through the interface to the person's nostril passages;
   monitoring the air pressure in the interface to detect an onset of sleep disorder breathing; then
   increasing the air pressure if the onset of sleep disorder breathing is detected while continuing to monitor the air pressure in the interface for the onset of sleep disorder breathing; and wherein the step of monitoring the air pressure in the interface comprises:
   sensing pressure waveforms resulting from the person's breathing;
   filtering the sensed waveforms to pass only frequencies of a selected range;
   determining a present energy level of each of the filtered waveforms;
   comparing the present energy level determined to an average energy level of previously filtered waveforms by the same person; and if the present energy level determined falls within a selected range based on the average energy level,
   counting the number of waveforms that fall within the range within a selected time period, and if the number is within a selected amount, then providing a signal to increase the air pressure.

2. A method for controlling sleep disorder breathing of a person, comprising:
   (a) connecting an interface from a source of air pressure to the person's nostril passages;
   (b) supplying air pressure from the source through the interface to the person's nostril passages;
   (c) monitoring the air pressure in the interface to detect snoring; then
   (d) increasing the air pressure if snoring is detected while continuing to monitor the air pressure in the interface for the continuance of snoring; then
   (e) after a selected time period, if snoring is still being detected, further increasing the air pressure; then
   (f) repeating step (e) until a maximum level of air pressure is reached; and
   (g) gradually reducing the air pressure after a selected time period if snoring is not detected; and wherein the step of detecting snoring comprises:
   sensing pressure waveforms in the interface occurring as a result of the person's breathing;
   filtering the sensed waveforms to pass only a selected frequency range of filtered waveforms associated with snoring;
   determining a present area for each of the filtered waveforms;
   determining a present duration for each of the filtered waveforms;
   computing an average area based on areas computed for a selected number of previous filtered waveforms of the same person;
   computing an average duration based on durations computed for a selected number of previous filtered waveforms of the same person;
   comparing the present area to the average area and comparing the present duration to the average duration; and if the present area and the present duration fall within selected ranges of the average area and average duration, counting the number of filtered waveforms that fall within the ranges within a selected time period, and if the number is within a selected amount, then increasing the air pressure.

3. A method for controlling sleep disorder breathing of a person, comprising:

(a) connecting an interface from a source of air pressure to the person's nostril passages;

(b) supplying air pressure from the source to the person's nostril passages;

(c) sensing pressure waveforms in the interface occurring as a result of the person's breathing;

(d) filtering the sensed waveforms to pass only filtered waveforms within a selected frequency range associated with snoring;

(e) determining selected values of the filtered waveforms and comparing the values to average values of waveforms associated with the person's snoring to determine if the filtered waveforms fall within a selected range;

(f) counting the number of filtered waveforms that fall within the range within a selected time period; and if the number is within a selected amount to indicate snoring associated with sleep disorder breathing, (g) increasing the air pressure; then (h) after a selected time period, further increasing the air pressure if snoring associated with sleep disorder breathing is still being detected while continuing to monitor the air pressure in the interface for the continuance of snoring; then (i) repeating step (h) until a selected maximum level of air pressure is reached; and (j) reducing the air pressure in a controlled manner to a selected minimum after a selected time period if snoring associated with sleep disorder breathing is not being detected.

4. The method according to claim 3 wherein step (e) comprises:

determining a present area for each of the filtered waveforms;

determining a present duration for each of the filtered waveforms;

computing an average area based on areas computed for a selected number of previous filtered waveforms of the same person;

computing an average duration based on durations computed for a selected number of previous filtered waveforms of the same person; and comparing the present area to the average area and comparing the present duration to the average duration to determine if the present area and the present duration fall within selected ranges of the average area and average duration.

5. An apparatus for controlling sleep disorder breathing of a person, comprising in combination:

a source of air pressure;

an interface having one end connected to the source of air pressure and another end adapted to fit over the person's nostril passages to supply air pressure from the source to the person's nostril passages;

means for monitoring the air pressure in the interface to detect an onset of sleep disorder breathing;

means for automatically increasing the air pressure if the onset of sleep disorder breathing is detected;

and wherein the means for monitoring the air pressure in the interface comprises:

means for sensing pressure waveforms resulting from the person's breathing;

means for filtering theسنsed waveforms to pass only frequencies of a selected range;

means for determining a present energy level of each of the filtered waveforms;

means for comparing the present energy level determined to an average energy level of previously filtered waveforms by the same person, and for determining if the present energy level determined falls within a selected range based on the average energy level; and means for counting the number of filtered waveforms that fall within the range within a selected time period, and if the number is within a selected amount, then for providing increasing the air pressure.

6. An apparatus for controlling sleep disorder breathing of a person, comprising in combination:

a source of air pressure;

an interface having one end connected to the source of air pressure and another end adapted to fit over the person's nostril passages to supply air pressure from the source to the person's nostril passages;

means for sensing the air pressure waveforms in the interface which occur as a result of the person's breathing;

means for determining if the waveforms sensed have snoring characteristics associated with waveforms that occur during snoring;

means for increasing the air pressure if waveforms are sensed which have snoring characteristics and for gradually reducing the air pressure after a selected time period of waveforms with snoring characteristics cease to exist; and wherein the means for determining if the waveforms sensed have snoring characteristics filters waveforms sensed and passes only those within a selected frequency range and further comprises:

means for determining a present energy level of each of the filtered waveforms;

means for comparing the present energy level determined to an average energy level of previously filtered waveforms by the same person and for determining if the present energy level determined falls within a selected range based on the average energy level; and means for counting the number of filtered waveforms that fall within the range within a selected time period, and if the number is within a selected amount, then for providing a signal to increase the air pressure.

7. An apparatus for controlling sleep disorder breathing of a person, comprising in combination:

a source of air pressure;

an interface having one end connected to the source of air pressure and another end adapted to fit over the person's nostril passages to supply air pressure from the source to the person's nostril passages;

means for sensing the air pressure waveforms in the interface which occur as a result of the person's breathing;

means for determining if the waveforms sensed have snoring characteristics associated with waveforms that occur during snoring;

means for increasing the air pressure if waveforms are sensed which have snoring characteristics and for gradually reducing the air pressure after a selected time period of waveforms with snoring characteristics cease to exist; and wherein the means for determining if the waveforms sensed have snoring characteristics filters waveforms sensed and passes only those within a selected frequency range and further comprises:

means for determining a present area for each of the filtered waveforms;

means for determining a present duration for each of the filtered waveforms;

means for computing an average area based on areas computed for a selected number of previous filtered waveforms of the same person;

means for computing an average duration based on durations computed for a selected number of previous filtered waveforms of the same person; and means for comparing the present area to the average area and comparing the present duration to the average duration to determine if the present area and the present duration fall within selected ranges of the average area and average duration.

* * * * *

UNITED STATES PATENT AND TRADEMARK OFFICE
CERTIFICATE OF CORRECTION

PATENT NO. : 5,203,343
DATED : April 20, 1993
INVENTOR(S) : John R. Axe, et al

It is certified that error appears in the above-indentified patent and that said Letters Patent is hereby corrected as shown below:

On the title page, After Item [73] Assignee: Add "of inventors Fu-Chung Yen and Khosrow Behbehani"

Signed and Sealed this

Thirty-first Day of May, 1994

Attest:

BRUCE LEHMAN

Attesting Officer

Commissioner of Patents and Trademarks